United States Patent [19]

Au-Young et al.

[11] Patent Number: 5,798,246

[45] Date of Patent: Aug. 25, 1998

[54] CYCLIC NUCLEOTIDE PHOSPHODIESTERASE

[75] Inventors: Janice Au-Young, Berkeley; Benjamin Graeme Cocks, Palo Alto; Roger Coleman, Mountain View; Jeffrey J. Seilhamer, Los Altos Hills, all of Calif.

[73] Assignee: Incyte Pharmaceuticals, Inc., Palo Alto, Calif.

[21] Appl. No.: 624,663

[22] Filed: Mar. 25, 1996

[51] Int. Cl.$^6$ .............................. C12N 9/18; C12N 15/12; C12N 15/52; C12N 15/85

[52] U.S. Cl. .................. 435/196; 435/172.3; 435/320.1; 435/325; 536/23.2; 536/23.5

[58] Field of Search ............................ 536/23.2, 23.5; 435/325, 320.1, 69.1, 172.3, 197

[56] References Cited

PUBLICATIONS

Angel, J.B. et al., "Rolipram, a specific type IV phosphodiestesterase inhibitor, is a potent inhibitor of HIV–1 replication", *AIDS* (1995) 9:1137–1144.

Bang, Y.J. et al., "Terminal neuroendocrine differentiation of human prostate carcinoma cells in response to increased intracellular cyclic AMP", *Proc Natl Acad Sci USA* (1994) 91:5330–5334.

Banner, K.H. and Page, C.P., "Immunomodulatory actions of xantines and isoenzyme selective phosphodiesterase inhibitors", *Mondaldi Arch Chest Dis* (1995) 50:4,286–292.

Banner, K.H. and Page, C.P., "Theophylline and selective phosphodiesterase inhibitors as anti–inflammatory drugs in the treatment of bronchial asthma", *Eur Respir J* (1995) 8:996–1000.

Beavo, Joseph A., "Cyclic Nucleotide Phosphodiesterases: Functional Implications of Multiple Isoforms", *Physiological Reviews* (1995) 75:725–747.

Deonarain, M.P. and Epenetos, A.A., "Targeting enzymes for cancer therapy: old enzymes in new roles", (1994) *Br J Cancer* 70:786–794.

Joulain, C. et al., "Influence of polyunsaturated fatty acids on lipid metabolism in human blood mononuclear cells and early biochemical events associated with lymphocyte activation", *J Lipid Mediators Cell Signalling* (1995) 11:63–79.

Matousovic, K. et al., "Inhibitors of Cyclic Nucleotide Phosphodiesterase Isozymes Type–III and Type–IV Suppress Mitogenesis of Rat Mesangial Cells", *J Clin Invest* (1995) 96:401–410.

Sasaki, H. et al., "Suppression of oro–facial movements by rolipram, a cAMP phosphodiesterase inhibitor, in rats chronically treated with haloperidol", *European Journal of Pharmacology* (1995) 282:71–76.

Sommer, N., "The antidepressant rolipram suppresses cytokine produciton and prevents autoimmune encephalomyelitis", *Nature Medicine* (1995) 1:244–248.

Thompson, W. J., "Cyclic Nucleotide Phosphodiesterases: Pharmacology, Biochemistry and Function", *Pharmac Ther* (1991) 51:13–33.

Verghese, M.W. et al., "Regulation of Distinct Cyclic AMP–Specific Phosphodiesterase (Phosphodiesterase Type 4) Isozymes in Human Monocytic Cells", *Molecular Pharmacology* (195) 47:1164–1171.

Hillier L. et al. "zh47a11.r1 Soares fetal liver spleen 1NFLS S1 Homo sapiens cDNA clone 415196 5" EST Accession No. W91922., Jul. 16, 1996.

*Primary Examiner*—Douglas M. Robinson
*Assistant Examiner*—Amy J. Nelson
*Attorney, Agent, or Firm*—Lucy J. Billings

[57] ABSTRACT

The present invention relates to a heretofore uncharacterized family of cyclic nucleotide phosphodiesterases (CN PCD8) and provides specific polynucleotide and amino acid sequences which encode and identify CN PDE8 family members designated herein as CN PDE8A and CN PDE8B. The present invention also relates to the use of proteins, peptides and organic molecules capable of modulating CN PDE8 activity to inhibit or enhance phosphodiesterase activity associated with disease. The present invention further relates to the use of CN PDE8 and genetically engineered host cells that express CN PDE8 to evaluate and screen for substances and compounds that modulate cyclic nucleotide phosphodiesterase activity. The present invention also provides for cn pde8 antisense molecules. The invention provides genetically engineered expression vectors and host cells for the production of purified CN PDE8 polypeptide. The present invention further provides pharmaceutical compositions and methods of treatment based on the identification of agonist, antagonists and inhibitors of CN PDE8. The invention specifically provides for use of the cn pde8 polynucleotide sequences as a diagnostic composition for the detection of disease.

7 Claims, 8 Drawing Sheets

```
          9              18              27       36              45              54
5' ATG GCC CGG ATA CAT TCC ATG ACA ATT GAG GCG CCC ATC ACC AAG GTA ATC AAT
   Met Ala Arg Ile His Ser Met Thr Ile Glu Ala Pro Ile Thr Lys Val Ile Asn 63             72              81       90              99             108
   ATT ATC AAT GCT GCC CAG GAA AGT CCC ATG AGT CCT GTG ACA GAA GCC CTA GAC
   Ile Ile Asn Ala Ala Gln Glu Ser Pro Met Ser Pro Val Thr Glu Ala Leu Asp 117            126             135      144             153             162
   CGT GTG CTG GAA ATT CTA AGA ACC ACT GAG TTA TAT TCA CCA CAG TTT GGT GCT
   Arg Val Leu Glu Ile Leu Arg Thr Thr Glu Leu Tyr Ser Pro Gln Phe Gly Ala 171            180             189      198             207             216
   AAA GAT GAT CCC CAT GCC AAT GAC CTT GTT GGG GGC TTA ATG TCT GAT GGT
   Lys Asp Asp Pro His Ala Asn Asp Leu Val Gly Gly Leu Met Ser Asp Gly 225            234             243      252             261             270
   TTG CGA AGA CTA TCA GGG AAT GAA TAT GTT CTT TCA ACA AAA AAC ACT CAA ATG
   Leu Arg Arg Leu Ser Gly Asn Glu Tyr Val Leu Ser Thr Lys Asn Thr Gln Met 279            288             297      306             315             324
   GTT TCA AGC AAT ATA ATC ACT CCC CTT GAT GAT GTC CCA CCA CGG ATA
   Val Ser Ser Asn Ile Ile Thr Pro Leu Asp Asp Val Pro Pro Arg Ile 333            342             351      360             369             378
   GCT CGG GCC ATG GAA AAT GAG GAA TAC TGG GAC TTT GAT ATT TTT GAA CTG GAG
   Ala Arg Ala Met Glu Asn Glu Glu Tyr Trp Asp Phe Asp Ile Phe Glu Leu Glu
```

FIGURE 1A

```
    387              396              405              414              423              432
GTT GCC ACC CAC AAT AGG CCT TTG ATT TAT CTT GGT CTC AAA ATG TTT GCT CGC
Val Ala Thr His Asn Arg Pro Leu Ile Tyr Leu Gly Leu Lys Met Phe Ala Arg 441              450              459              468              477              486
TTT GGA ATC TGT GAA TTC TTA CAC TGC TCC GAG TCA ACG CTA AGA TCA TGG TTA
Phe Gly Ile Cys Glu Phe Leu His Cys Ser Glu Ser Thr Leu Arg Ser Trp Leu 495              504              513              522              531              540
CAA ATT GAA GCC AAT TAT CAT CCT TCC AAT CCC TAC CAC AAT TCT ACA CAT
Gln Ile Glu Ala Asn Tyr His Ser Asn Pro Tyr His Asn Ser Thr His 549              558              567              576              585              594
TCT GCT GAT GTG CTT CAT GCC ACT GCC TAT TTT CTC TCC AAG AGG ATA AAG
Ser Ala Asp Val Leu His Ala Thr Ala Tyr Phe Leu Ser Lys Glu Arg Ile Lys 603              612              621              630              639              648
GAA ACT TTA GAT CCA ATT GAT GAG GTC GCT GCA CTC ATC GCA GCC ACC ATT CAT
Glu Thr Leu Asp Pro Ile Asp Glu Val Ala Ala Leu Ile Ala Ala Thr Ile His 657              666              675              684              693              702
GAT GTG GAT CAC CCT GGG AGA ACC AAC TCC TTC TGT AAT GCT GGA AGT GAG
Asp Val Asp His Pro Gly Arg Thr Asn Ser Phe Cys Asn Ala Gly Ser Glu 711              720              729              738              747              756
CTG GCC ATT TTG TAC AAT GAC ACT GCT GTG CTG GAG AGC CAC CAT GCG GCC TTG
Leu Ala Ile Leu Tyr Asn Asp Thr Ala Val Leu Glu Ser His His Ala Ala Leu
```

FIGURE 1B

```
        765            774            783            792            801            810
GCC TTC CAG CTG ACC ACT GGA GAT AAA TGC AAT ATA TTT AAA AAC ATG GAG
Ala Phe Gln Leu Thr Thr Gly Asp Lys Cys Asn Ile Phe Lys Asn Met Glu 819            828            837            846            855            864
AGG AAT GAT TAT CGG ACA CTG CGC CAG GGG ATT ATC GAC ATG GTC TTA GCC ACA
Arg Asn Asp Tyr Arg Thr Leu Arg Gln Gly Ile Ile Asp Met Val Leu Ala Thr 873            882            891            900            909            918
GAA ATG ACA AGG CAC TTT GAG CAT GTC AAC AAA TTT GTC AAC AGC ATC AAC AAA
Glu Met Thr Arg His Phe Glu His Val Asn Lys Phe Val Asn Ser Ile Asn Lys 927            936            945            954            963            972
CCC TTG GCA ACA CTA GAA GAA AAT GGG GAA ACT GAT AAA AAC CAG GAA GTG ATA
Pro Leu Ala Thr Leu Glu Glu Asn Gly Glu Thr Asp Lys Asn Gln Glu Val Ile 981            990            999            1008           1017           1026
AAC ACT ATG CTT AGG ACT CCA GAG AAC CGG ACC CTA ATC AAA CGA ATG CTG ATT
Asn Thr Met Leu Arg Thr Pro Glu Asn Arg Thr Leu Ile Lys Arg Met Leu Ile 1035           1044           1053           1062           1071           1080
AAA TGT GCT GAT GTG TCC AAT CCC TGC CGA CCC CTG CAG TAC TGC ATC GAG TGG
Lys Cys Ala Asp Val Ser Asn Pro Cys Arg Pro Leu Gln Tyr Cys Ile Glu Trp 1089           1098           1107           1116           1125           1134
GCT GCA CGC ATT TCG GAA GAA TAT TTT TCT CAG ACT GAT GAA GAG AAG CAG CAG
Ala Ala Arg Ile Ser Glu Glu Tyr Phe Ser Gln Thr Asp Glu Glu Lys Gln Gln
```

FIGURE 1C

```
     1143           1152           1161           1170           1179           1188
GGC TTA CCT GTG GTG ATG CCA GTG TTT GAC AGA AAT ACC TGC AGC ATC CCC AAA
Gly Leu Pro Val Val Met Pro Val Phe Asp Arg Asn Thr Cys Ser Ile Pro Lys 1197           1206           1215           1224           1233           1242
TCC CAA ATC TCT TTC ATT GAT TAC TTC ATC ACA GAC ATG TTT GAT GCT TGG GAT
Ser Gln Ile Ser Phe Ile Asp Tyr Phe Ile Thr Asp Met Phe Asp Ala Trp Asp 1251           1260           1269           1278           1287           1296
GCC TTT GTA GAC CTG CCT GAT TTA ATG CAG CAT CTT GAC AAC AAC TTT AAA TAC
Ala Phe Val Asp Leu Pro Asp Leu Met Gln His Leu Asp Asn Asn Phe Lys Tyr 1305           1314           1323           1332           1341
TGG AAA GGA CTG GAC GAA ATG AAG CTG CGG AAC CTC CGA CCA CCT CCT GAA TA 3'
Trp Lys Gly Leu Asp Glu Met Lys Leu Arg Asn Leu Arg Pro Pro Pro Glu
```

FIGURE 1D

```
     9              18              27              36              45              54
5' ATC AAC AAG CCA ATG GCA GCT GAG ATT GAA GGC AGC GAC TGT GAA TGC AAC CCT
   Ile Asn Lys Pro Met Ala Ala Glu Ile Glu Gly Ser Asp Cys Glu Cys Asn Pro 63              72              81              90              99             108
   GCT GGG AAG AAC TTC CCT GNA AAC CAA ATC CTG ATC AAA NGC ATG ATG ATT AAG
   Ala Gly Lys Asn Phe Pro Xxx Asn Gln Ile Leu Ile Lys Xxx Met Met Ile Lys 117             126             135             144             153             162
   TGT GCT GAN GNG GNC XXX XXX CCA TGC CGA CCC TTG GAC CTG TGC ATT GAA TGG GCT
   Cys Ala Xxx Xxx Xxx Xxx Xxx Pro Cys Arg Pro Leu Asp Leu Cys Ile Glu Trp Ala 171             180             189             198             207             216
   GGG AGG ATC TCT GAG GAG TAT TTT GCA CAG ACT GAT GAA GAG AAG AGA CAG GGA
   Gly Arg Ile Ser Glu Glu Tyr Phe Ala Gln Thr Asp Glu Glu Lys Arg Gln Gly 225             234             243
   CTA CCT GTG GTG ATG NCA GTG TTT GAC C 3'
   Leu Pro Val Val Met Xxx Val Phe Asp
```

FIGURE 2

CYCLIC NUCLEOTIDE PHOSPHODIESTERASE

FIELD OF THE INVENTION

The present invention relates generally to the field of molecular biology and specifically to a new family of cyclic nucleotide phosphodiesterases. The present invention further relates to novel nucleic acid and amino acid sequences of cyclic nucleotide phosphodiesterases and to their use in the diagnosis and treatment of disease. The present invention further relates to the use of the novel cyclic nucleotide phosphodiesterase and genetically engineered host cells that express the novel cyclic nucleotide phosphodiesterase to evaluate and screen for substances and compounds that modulate cyclic nucleotide phosphodiesterase activity.

BACKGROUND

Cyclic nucleotide phosphodiesterases (CN PDE) show specificity for purine cyclic nucleotide substrates and catalyze cyclic AMP (cAMP) and cyclic GMP (cGMP) hydrolysis (Thompson W. J. 1991 *Pharmac Ther* 51:13–33). CN PDEs regulate the steady-state levels of cAMP and cGMP and modulate both the amplitude and duration of cyclic nucleotide signal. At least seven different but homologous gene families of CN PDEs are currently known to exist in mammalian tissues. Most families contain distinct genes many of which are expressed in different tissues as functionally unique alternative splice variants. (Beavo 1995 *Physiological Reviews* 75:725–748).

All CN PDEs contain a core of about 270 conserved amino acids in the COOH-terminal half of the protein thought to be the catalytic domain of the enzyme. A conserved motif of the sequence HDXXHXXXXN has been identified in the catalytic domain of all CN PDEs isolated to date. The CN PDEs within each family display about 65% amino acid homology and the similarity drops to less than 40% when compared between different families with most of the similarity occurring in the catalytic domains.

Most cyclic nucleotide CN PDE genes have more than one alternatively spliced mRNA transcribed from them and in many cases the alternative splicing appears to be highly tissue specific providing a mechanism for selective expression of different CN PDEs (Beavo 1995 supra). Cell type specific expression suggests that the different isozymes are likely to have different cell type specific properties.

Type 1 CN PDEs are $Ca^{2+}$/calmodulin dependent, are reported to contain three different genes each of which appears to have at least two different splice variants, and have been found in the lung, heart and brain. Some of the calmodulin-dependent PDEs are regulated in vitro by phosphorylation/dephosphorylation events. The effect of phosphorylation is to decrease the affinity of the enzyme for calmodulin, which decreases PDE activity thereby increasing the steady state level of cAMP. Type 2 CN PDEs are cGMP stimulated, are localized in the brain and are thought to mediate the effects of cAMP on catecholamine secretion. Type 3 CN PDEs are cGMP inhibited, have a high specificity for cAMP as a substrate, and are one of the major PDE isozymes present in vascular smooth muscle and play a role in cardiac function. One isozyme of type 3 is regulated by one or more insulin-dependent kinases. Type 4 CN PDEs are the predominant isoenzyme in most inflammatory cells, with some of the members being activated by cAMP-dependent phosphorylation. Type 5 CN PDEs have traditionally been thought of as regulators of cGMP function but may also affect cAMP function. High levels of type 5 CN PDEs are found in most smooth muscle preparations, platelets and kidney. Type 6 CN PDE family members play a role in vision and are regulated by light and cGMP. A Type 7 CN PDE family member is found in high concentrations in skeletal muscle. A listing of CN PDE families 1–7, their localization and physiological role is given in Beavo 1995 supra.

Many functions of the immune and inflammatory responses are inhibited by agents that increase intracellular levels of cAMP (Verghese 1995 *Mol Pharmacol* 47:1164–1171) while the metabolism of cGMP is involved in smooth muscle, lung and brain cell function (Thompson W. 1991 *Pharmac Ther* 51:13–33). A variety of diseases have been attributed to increased CN PDE activity which results in decreased levels of cyclic nucleotides. For example, one form of diabetes insipidus in the mouse has been associated with increased PDE4 activity and an increase in low-$K_m$ cAMP PDE activity has been reported in leukocytes of atopic patients. Defects in CN PDE have also been associated with retinal disease. Retinal degeneration in the rd mouse, human autosomal recessive retinitis pigmentosa, and rod/cone dysplasia 1 in Irish Setter dogs has been attributed to mutations in the PDE6B gene. PDE3 has been associated with cardiac disease.

Many inhibitors of different CN PDEs have been identified and some have undergone clinical evaluation. For example, PDE3 inhibitors are being developed as antithrombotic agents, as antihypertensive agents and as cardiotonic agents useful in the treatment of congestive heart failure. Rolipram, a PDE4 inhibitor, has been used in the treatment of depression and other inhibitors of PDE4 are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al. 1995 *AIDS* 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al., 1995 *Nat Med* 1:244–248) and may be effective in the treatment of tardive dyskinesia (Sasaki et al, 1995 *Eur J Pharmacol* 282:71–76).

There are also nonspecific PDE inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al. 1995 *Eur Respir J* 8:996–1000) where it is thought to act by inhibiting both CN PDE cAMP and cGMP hydrolysis (Banner et al 1995 *Monaldi Arch Chest Dis* 50:286–292). Pentoxifylline, also known to block TNF-alpha production, may inhibit HIV-1 replication (Angel et al supra). A list of CN PDE inhibitors is given in Beavo 1995 supra.

CN PDEs have also been reported to effect cellular proliferation of a variety of cell types and have been implicated in the treatment of various cancers. Bang et al (1994 *Proc Natl Acad Sci USA* 91:5330–5334) reported that the prostate carcinoma cell lines DU 145 and LNCaP were growth inhibited by delivery of cAMP derivatives and phosphodiesterase inhibitors and observed a permanent conversion in phenotype from epithelial to neuronal morphology; Matousovic et al (1995 *J Clin Invest* 96:401–410) suggest that CN PDE isozyme inhibitors have the potential to regulate mesangial cell proliferation; Joulain et al (1995 *J Mediat Cell Signal* 11:63–79) reports that CN PDE has been shown to be an important target involved in the control of lymphocyte proliferation; and Deonarain et al (1994 *Br J Cancer* 70:786–94) suggest a tumor targeting approach to cancer treatment that involves intracellular delivery of phosphodiesterases to particular cellular compartments resulting in cell death.

The discovery of novel cyclic nucleotide phosphodiesterases will aid in the development of more specific and safer drug therapy.

SUMMARY

The present invention relates generally to a heretofore uncharacterized cyclic nucleotide phosphodiesterase family, designated herein as type 8 family (CN PDE8), and specifically to the two distinct family members designated, CN PDE8A and CN PDE8B (SEQ ID NO:2 and SEQ ID NO:4, respectively). The polynucleotide sequence of CN PDE8 has been identified among the polynucleotide sequences of cDNA libraries made from human fetal liver-spleen tissue, THP-1 cells, T and B lymphoblasts from a leukemic source and non adherent peripheral blood mononuclear cells, and the present invention relates to the use of the nucleotide and amino acid sequences of CN PDE8A in the study, diagnosis and treatment of disease states related to inflammation, conditions associated with proliferating hematopoietic cells, such as cancer, HIV infection, acute and chronic infection and immunosuppression.

The CN PDE8A nucleotide and amino acid sequences disclosed herein and genetically engineered host cells containing the CN PDE8A nucleotide and amino acid sequences may be used in screening methods for the detection of antagonists and inhibitors of CN PDE8A which may be used in the treatment of diseases associated with inflammation, conditions associated with proliferating hematopoietic cells, such as cancer and HIV infection. Alternatively, agonists or other molecules capable of elevating CN PDE 8 levels may be used to treat conditions related to immunosuppression, such as in Severe Combined Immunodeficiency Disease (SCID), or drug induced immunosuppression, such as found with chemotherapy and cyclosporin therapy for individuals undergoing organ or tissue transplant; or other conditions where it would be desirable to boost the immune response, such as in bacterial or fungal infection, eg *Staphylococcal aureus* infections.

The nucleotide acid sequence of cn pde8a (SEQ ID NO:1) and the protein it encodes, CN PDE8A (SEQ ID NO:2) is disclosed herein in FIGS. 1A,1B,1C,1D. The nucleotide sequence of cn pde8B (SEQ ID NO:3) and the protein it encodes, CN PDE 8B (SEQ ID NO:4) is disclosed herein in FIG. 2.

The present invention is based in part on the amino acid homology that CN PDE8A shares with known cyclic nucleotide phosphodiesterases, particularly in the conserved COOH terminus, and the presence of the motif "HDXX-HXXXXN" which has been found in the catalytic domain of all PDEs isolated to date. The present invention is also based upon the discovery that CN PDE8A has an expression pattern similar to the type 4 family of cyclic nucleotide phosphodiesterases, ie. expressed in tissues associated with inflammation and immunomodulation, but differs because it lacks the level of nucleotide homology typical for type 4 family members. The present invention is also based upon the identification of a nucleotide sequence, cn pde8b, in a cDNA library made from normal cardiac tissue, the amino acid sequence of which shares 75% amino acid homology with CN PDE8A and 38% amino acid homology with known phosphodiesterases in the 3' conserved region, indicating that CN PDE8A and B are members of a heretofore uncharacterized phosphodiesterase family.

The present invention is therefore based in part on the discovery that CN PDE8A is associated with inflammation, chronic and acute infection, conditions associated with proliferating hematopoietic cells, such as cancer, HIV infection and immunosuppression. CN PDE8A, and nucleotide sequences that encode it and oligonucleotides, peptide nucleic acid (PNA), fragments, portions or antisense molecules thereof, provide the basis for diagnostic methods for the early and accurate detection and/or quantitation of a CN PDE8 associated with asthma, septic shock, Alzheimer's disease, osteoarthritis and artherosclerosis, ischemia, psoriasis, lymphomatoid granulomatosis, allergies, leukemias and myeloproliferative diseases, HIV infection and autoimmune diseases, such as rheumatoid arthritis, myastenia gravis and diabetes and conditions related to immunosuppression, such as severe combined immunodeficiency (SCID). For example, the nucleotide sequence for cn pde 8a disclosed herein, or fragments thereof, may be used in hybridization assays of biopsied cells or tissues or bodily fluids to diagnose abnormalities in cn pde8 gene expression in individuals having or at risk for leukemia.

An abnormal level of nucleotide sequences encoding a CN PDE8 in a biological sample may reflect a chromosomal aberration, such as a nucleic acid deletion or mutation. Accordingly, nucleotide sequences encoding a CN PDE8 provide the basis for probes which can be used diagnostically to detect chromosomal aberrations such as deletions, mutations or chromosomal translocations in the gene encoding CN PDE. Cn pde8 gene expression may be altered in such disease states or there may be a chromosomal aberration present in the region of the gene encoding a CN PDE8.

A cn pde8 nucleic acid antisense molecule may be used to block the activity of the CN PDE8 in conditions where it would be preferable to elevate cyclic nucleotide levels, such as in the treatment of diseases associated with proliferating hematopoietic cells, such as chronic and acute leukemia.

The present invention also relates to the use of genetically engineered host cells expressing a CN PDE8 or variant thereof in screening methods for the identification of inhibitors and antagonists of the CN PDE8 that would modulate phosphodiesterase activity thereby modulating cyclic nucleotide levels. Such genetically engineered host cells could be used to screen peptide libraries or organic molecules capable of modulating CN PDE activity.

Antagonists and inhibitors of a CN PDE8, such as antibodies, peptides or small organic molecules, will provide the basis for pharmaceutical compositions for the treatment of diseases associated with asthma, Alzheimer's disease, osteoarthritis and artherosclerosis, ischemia, psoriasis, lymphomatoid granulomatosis, allergies, leukemias and myeloproliferative diseases, HIV infection and autoimmune diseases, such as rheumatoid arthritis, myastenia gravis and diabetes. Such inhibitors or antagonists can be administered alone or in combination with other therapeutics for the treatment of such diseases.

Alternatively, agonists or other agents capable of elevating levels of a CN PDE8 may be administered to individuals having conditions associated with immunosuppression, such as Severe Combined Immunodeficiency Disease (SCID), drug induced immunosuppression eg chemotherapy and cyclosporin therapy for individuals undergoing organ or tissue transplant; and acute or chronic infections, such as bacterial and fungal infections, including Staphylococcal and Aspergillus infections.

The present invention also relates, in part, to expression vectors and host cells comprising polynucleotide sequences encoding a CN PDE8 for the in vivo or in vitro production of a CN PDE8 protein.

Additionally, the present invention relates to the use of a CN PDE8 polypeptide, or fragment or variant thereof, to produce anti-CN PDE8 antibodies and to screen for antagonists or inhibitors of the CN PDE8 polypeptide which can be used diagnostically to detect and quantitate CN PDE8 protein levels in disease states.

The present invention also relates to pharmaceutical compositions comprising effective amounts of inhibitors or antagonists of a CN PDE8 protein or anti-sense nucleic acid encoding a CN PDE8 for the treatment of inflammation, conditions associated with proliferating hematopoietic cells and HIV infection. The present invention also relates to pharmaceutical compositions comprising effective amounts of agonists of a CN PDE8 or other molecule capable of elevating CN PDE8 levels for use in treating conditions associated with immunosuppression and acute and chronic infections. The present invention further relates to pharmaceutical compositions comprising effective amounts of cn pde8 polynucleotide sequences for use in treating individuals having solid tumors.

The invention further provides diagnostic assays and kits for the detection of a CN PDE8 in cells and tissues comprising a purified CN PDE8 which may be used as a positive control, and anti-CN PDE8 antibodies. Such antibodies may be used in solution-based, membrane-based, or tissue-based technologies to detect any disease state or condition related to the expression of CN PDE8 protein or expression of deletions or variants thereof.

DESCRIPTION OF THE FIGURES

FIGS. 1A,1B,1C and 1D display the polynucleotide (SEQ ID NO:1)and deduced amino acid (SEQ ID NO:2) sequence for CN PDE8A. Sequences shown in this Figure and FIG. 2 were produced using the multisequence alignment program of DNASTAR software (DNASTAR Inc. Madison Wis.). The motif "HDXXHXXXXN" is underlined.

FIG. 2 displays the polynucleotide (SEQ ID NO:3) and deduced amino acid (SEQ ID NO:4) sequence for CN PDE8B.

DETAILED DESCRIPTION OF THE INVENTION

Figure 4:
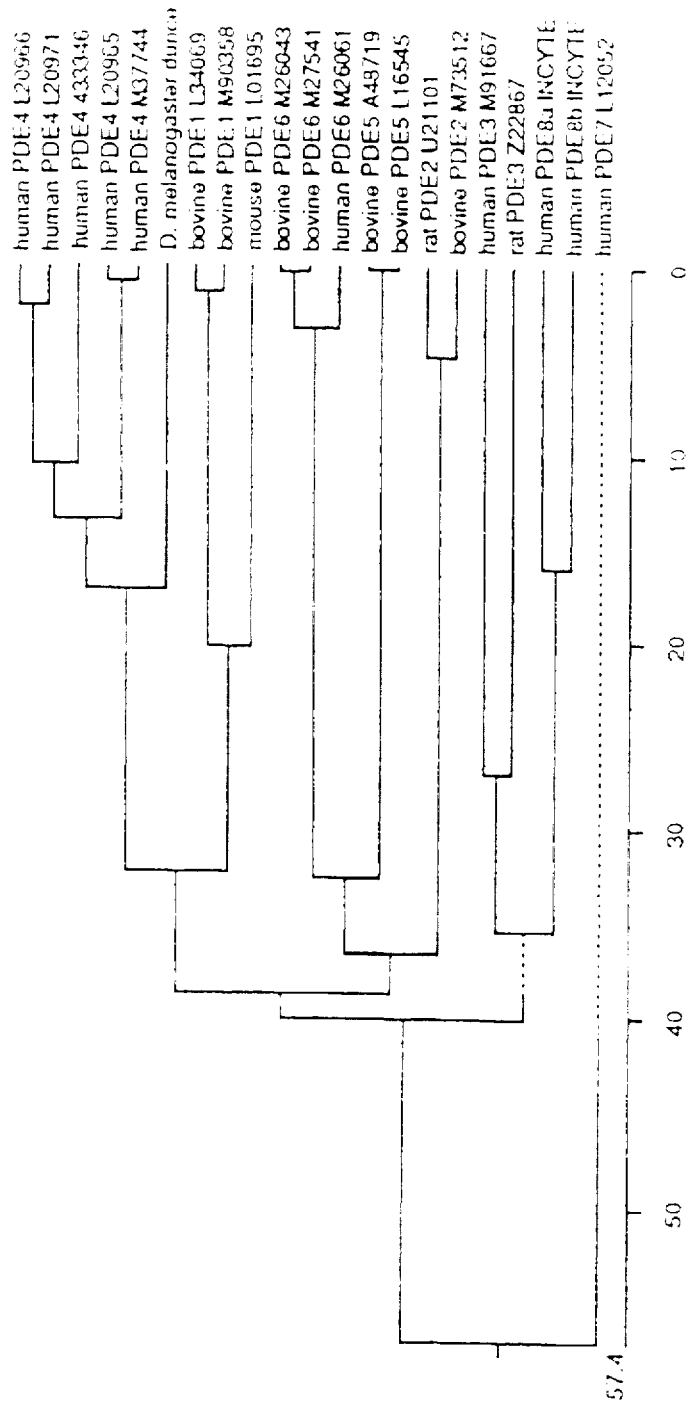
FIG. 4 displays a phylogenetic tree of CN PDE8A and CN PDE8B along with known cyclic nucleotide phosphodiesterases generated by the phylogenetic tree program of DNAstar software using the Clustal method with the PAM250 residue weight table.

The present invention relates generally to a heretofore uncharacterized cyclic nucleotide phosphodiesterase family and specifically to two distinct family members designated, CN PDE8A and CN PDE8B. As illustrated in FIG. 4, which presents a phylogenetic tree of cyclic phosphodiesterases, CN PDE8A and CN PDE8B are distinct from known cyclic nucleotide phosphodiesterases and related to one another. The present invention is based in part on the amino acid homology that CN PDE8A and CN PDE8B share with known cyclic nucleotide phosphodiesterases and the ability of known cyclic nucleotide PDEs to hydrolyse cAMP and cGMP and to be regulated by cellular events.

The present invention is also based in part on the presence of nucleotide sequences encoding CN PDE8A in random samples of about 2500 to 4400 usable sequences in cDNA libraries made from human fetal liver-spleen tissue (INCYTE library SPLNFET01), THP-1 cells, the human promonocyte line derived from the peripheral blood of an individual subject to acute monocytic leukemia (ATCC accession number TIB 202(INCYTE library THP1PLB02), T and B lymphoblasts from a leukemic source (INCYTE library TBLYNOT01) and non adherent peripheral blood mononuclear cells (INCYTE libraries TLYMNOT02 and TMLR3DT01), cell sources containing rapidly proliferating cells or that are involved in inflammation or immunomodulation. The present invention is also based upon the presence of a related nucleotide sequence encoding a CN PDE8B in random samples of about 3800 usable sequences in a cDNA library made from the left atrium of the heart.

The present invention is based therefore on the discovery of novel CN PDE8A from a heretofore uncharacterized cyclic nucleotide phosphodiesterase family that is associated with inflammation and/or immunomodulation. CN PDE8A and B, and nucleic acid sequences that encode it and oligonucleotides, peptide nucleic acid (PNA), fragments, portions or antisense molecules thereof, provide the basis for diagnostic methods for the early and accurate detection and/or quantitation of CN PDE8A associated with inflammation, chronic and acute infection, conditions associated with proliferating hematopoietic cells, such as cancer, HIV infection and immunosuppression.

Furthermore, the nucleotide sequences disclosed herein may be used in the detection of aberrations, such as mutations and deletions, in the gene encoding a CN PDE8. For example, the nucleotide sequences disclosed herein may be used to identify and isolate a genomic sequence for a CN PDE8. PCR primers can be designed from various portions of the introns and exons of a genomic CN PDE8 that will allow detection of aberrations in the genomic sequence.

The present invention further relates to the use of CN PDE8A and CN PDE8B and genetically engineered host cells that express CN PDE8A and CN PDE8B to evaluate and screen for substances and compounds that modulate cyclic nucleotide phosphodiesterase activity. Such screening methods may be used for the identification of allosteric agonists and antagonists of phosphodiesterase activity as well as for the identification of inhibitors of cyclic nucleotide hydrolysis.

Antagonists and inhibitors of a CN PDE8 or a cn pde8 antisense molecule will provide the basis for pharmaceutical compositions for the treatment and amelioration of symptoms associated with inflammation, proliferation of hematopoietic cells and HIV infection. Agonists of a CN PDE8 will provide the basis of the treatment and amelioration of symptoms associated with acute and chronic infection and immunosuppression. For example, administration of antagonists or inhibitors of a CN PDE8 or an antisense CN PDE8 molecule may alleviate the symptoms associated with inflammation such as swelling and pain.

For example, antagonists or inhibitors of a CN PDE8 may be administered to diminish the levels of cytokines, such as TNF-alpha and beta, interferon gamma, interleukins and chemokines that are involved in the response to inflammation. Antagonists of a CN PDE8 may also be used in the treatment of HIV-1 infection where it would be desirable to diminish the level of TNF-alpha which has been associated with enhanced HIV replication.

"Nucleic acid sequence" as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. As used herein "amino acid sequence" refers to peptide or protein sequences or portions thereof. As used herein, lower case "cn pde" refers to a nucleic acid sequence whereas upper case "CN PDE" refers to a protein sequence. As used herein, peptide nucleic acid (PNA) refers to a class of informational molecules that have a neutral "peptide like" backbone with nucleobases that allow molecules to hybridize to complementary DNA or RNA with higher affinity and specificity than corresponding oligonucleotides (PerSeptive Biosystems 1-800-899-5858).

As used herein, CN PDE8 refers to a family of CN PDEs heretofore uncharacterized having members represented by CN PDE 8A and 8B from bovine, ovine, murine, porcine, equine and preferably human sources, in naturally occurring or in variant form, or from any source, whether natural, synthetic, semi-synthetic or recombinant.

As used herein, "naturally occurring" refers to a CN PDE8 with an amino acid sequence found in nature, and "biologically active" refers to a CN PDE8 having structural, regulatory or biochemical functions of the naturally occurring CN PDE8. Specifically, a CN PDE8 of the present invention has the ability to hydrolyze a cyclic nucleotide. As used herein, "immunological activity" is defined as the capability of the natural, recombinant or synthetic CN PDE8 or any oligopeptide thereof, to induce a specific immune response in appropriate animals or cells and to bind with specific antibodies.

The term "derivative" as used herein refers to the chemical modification of a CN PDE8. Illustrative of such modifications would be replacement of hydrogen by an alkyl, acyl, or amino group. A CN PDE8 polypeptide derivative would encode a polypeptide which retains essential biological characteristics of a naturally occurring CN PDE8.

As used herein, the term "purified" refers to molecules, either nucleic or amino acid sequences, that are removed from their natural environment and isolated or separated from at least one other component with which they are naturally associated.

The Cn pde Coding Sequences

The nucleotide sequences of cn pde 8a (SEQ ID NO:1) and cn pde 8b (SEQ ID NO:3) are shown in FIGS. 1 and 2 respectively. The present invention encompasses nucleotide sequences encoding any member from the CN PDE8 family which would include nucleotide sequence having at least 40% homology and preferably at least 50% homology to the entire nucleotide sequence of SEQ ID NO:1. A partial coding region for CN PDE8A was initially identified within a cDNA library made from THP-1 cells where it was found 1 time in 2500 usable sequences. A BLAST search (Basic Local Alignment Search Tool; Altschul S.F. (1993) J. Mol. Evol. 36:290–300; Altschul S. F. et al (1990) J. Mol. Biol. 215:403–410) comparing the cDNAs of the THP-1 library (INCYTE library THP1PLB02) against the primate database of GenBank 91 identified Incyte Clone 156196 as a non-exact match to rat cn pde (NCBI GI 409816) which appears to be a member of family 3 or 4 cyclic phosphodiesterases. Polynucleotide sequences encoding CN PDE were subsequently found in a cDNA library made from human fetal spleen/liver tissue where it was found 1 time in about 2800 usable sequences and non-adherent peripheral blood mononuclear cells (PBMN) where it was found 1 time in 3941 usable sequences. A partial coding region for CN PDE8B was identified within a cDNA library made from heart tissue where it was found 1 time in about 3800 usable sequences. As used herein term "usable sequences" refers to the total number of clones in a library after the removal of vector, nucleotide repeats, contamination, and mitochondrial DNA.

Figure 3A:
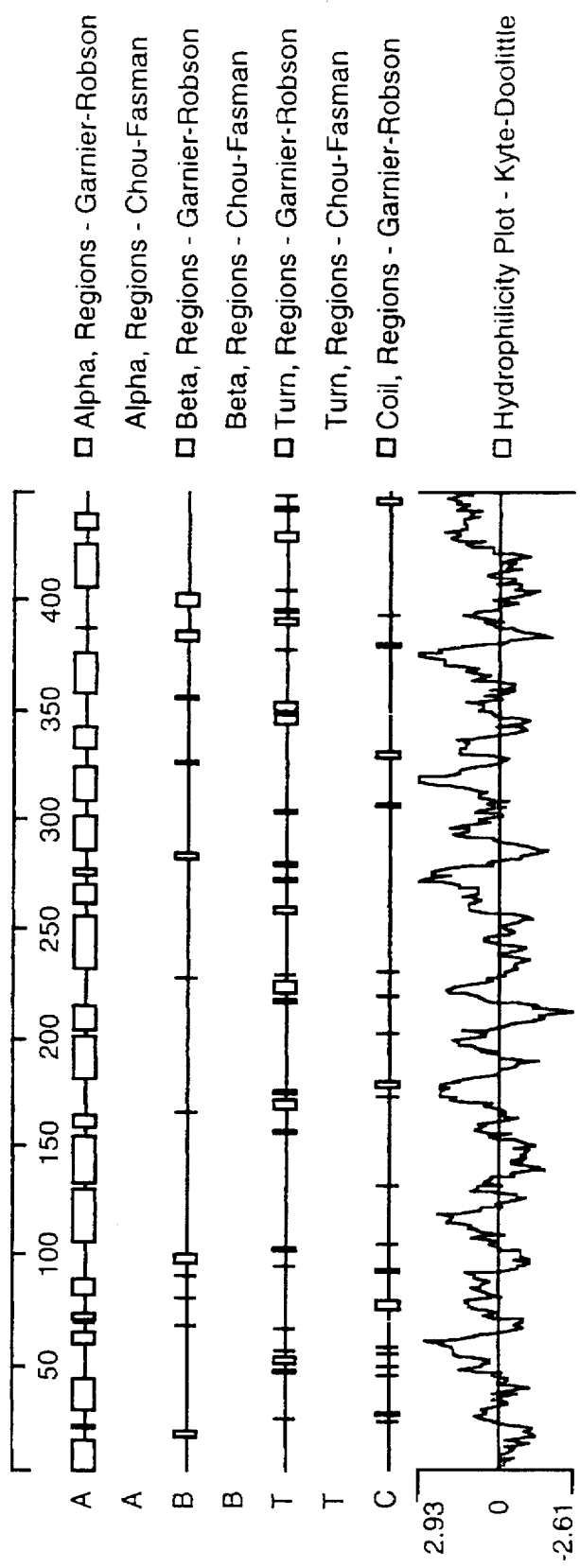
FIGS. 3A and 3B display an analysis of the hydrophobicity characteristics of CN PDE8A based on the predicted amino acid sequence and comparison.
Figure 3B:
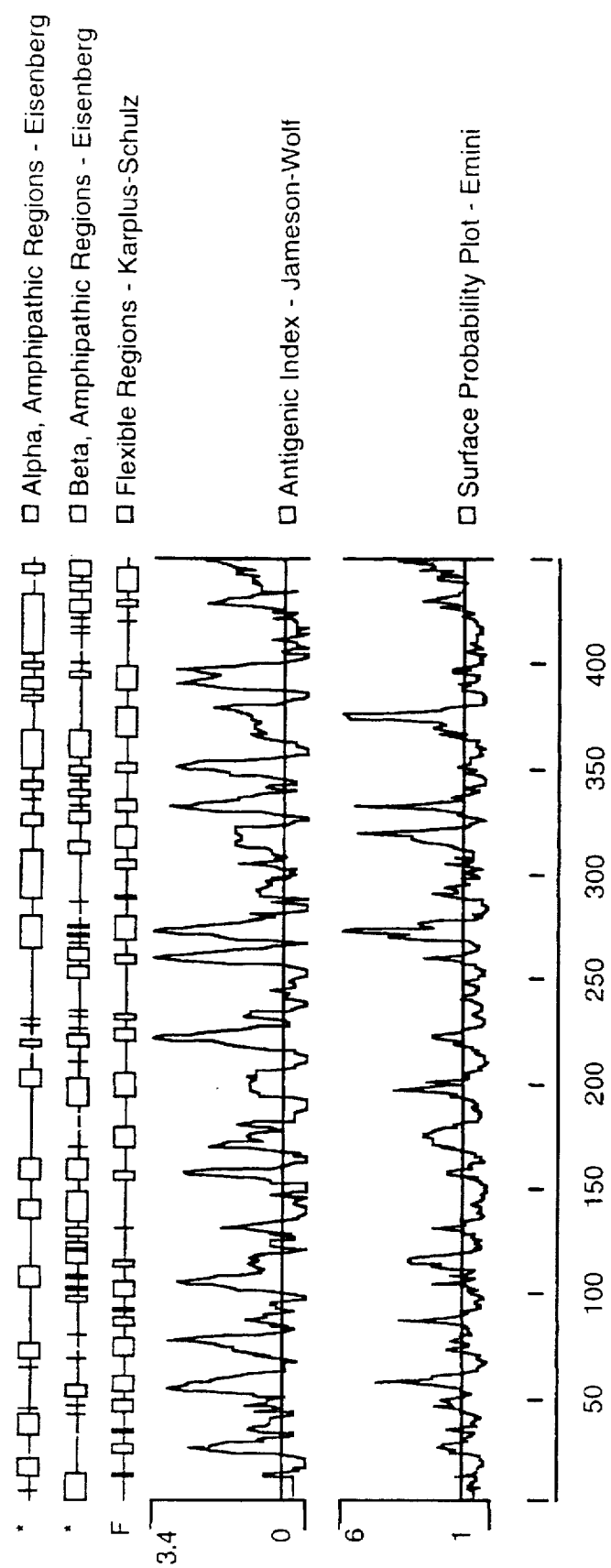

The nucleotide sequence of SEQ ID NO:1 encodes a CN PDE8A amino acid sequence (SEQ ID NO:2) having 449 residues with the phosphodiesterase catalytic motif HDVDHPGRTN occurring at residue position 200–209 inclusive of SEQ ID NO:2. As illustrated in FIGS. 3A and 3B, CN PDE8A contains alternating hydrophilic and hydrophobic primary structure. The partial nucleotide sequence of SEQ ID NO:3 encodes a CN PDE8B fragment which has 75% identity to CN PDE 8A. The entire coding region of cn pde8b can be determined through techniques known to those of skill in the art.

Methods for DNA sequencing are well known in the art and employ such enzymes as the Klenow fragment of DNA polymerase 1, EQUENASE® (US Biochemical Corp, Cleveland, Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Methods to extend the DNA from an oligonucleotide primer annealed to the DNA template of interest have been developed for both single-stranded and double-stranded templates. Chain termination reaction products were separated using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton Micro Lab 2200 (Hamilton, Reno Nev.), Peltier Thermal Cycler (PTC200; MJ Research, Watertown Mass.) and the ABI Catalyst 800 and 377 and 373 DNA sequencers (Perkin Elmer, Norwalk Conn.).

The quality of any particular cDNA library from which polynucleotides encoding CN PDE are found may be determined by performing a pilot scale analysis of the cDNAs and checking for percentages of clones containing vector, lambda or E. coli DNA, mitochondrial or repetitive DNA, and clones with exact or homologous matches to public databases.

Extending Cn pde Polynucleotide Sequence

The polynucleotide sequence of a cn pde8 may be extended utilizing the nucleotide sequences from SEQ ID NO:1 in various methods known in the art to detect upstream sequences such as promoters and regulatory elements. Gobinda et al (1993; PCR Methods Applic 2:318–22) disclose "restriction-site polymerase chain reaction (PCR)" as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T.

et al (1988) Nucleic Acids Res 16:8186). The primers may be designed using Oligo 4.0 (National Biosciences Inc. Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al (1991) PCR Methods Applic 1:111–19) is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR.

Parker J. D. et al (1991; Nucleic Acids Res 19:3055–60), teach walking PCR, a method for targeted gene walking which permits retrieval of unknown sequence. PROMOTER FINDER™ is a new kit available from Clontech (Palo Alto Calif.) which uses PCR, nested primers and special libraries to "walk in" genomic DNA. This process avoids the need to screen libraries and is useful in finding intron/exon junctions.

Another PCR method, "*Improved Method for Obtaining Full Length cDNA Sequences*" by Guegler et al, patent application Ser. No 08/487,112, filed Jun. 7, 1995, now abandoned and hereby incorporated by reference, employs XL-PCR™ enzymes (Perkin-Elmer, Foster City Calif.) to amplify and/or extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for obtaining introns and extending 5' sequence.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER™ and SEQUENCE NAVIGATOR™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851-8).

Expression Systems

In accordance with the present invention, cn pde8 polynucleotide sequences which encode CN PDE8, fragments of the polypeptide, fusion proteins or functional equivalents thereof, may be used to generate recombinant DNA molecules that direct the expression of CN PDE8 in appropriate host cells. Due to the inherent degeneracy of the genetic code, other DNA sequences which encode substantially the same or a functionally equivalent amino acid sequence, may be used to clone and express CN PDE8. As will be understood by those of skill in the art, it may be advantageous to produce CN PDE-encoding nucleotide sequences possessing non-naturally occurring codons. Codons preferred by a particular prokaryotic or eukaryotic host (Murray E. et al (1989) Nuc Acids Res 17:477–508) can be selected, for example, to increase the rate of CN PDE8 expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIGS. 1A,1B,1C and 1D under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences. The term "hybridization" as used herein shall include "the process by which a strand of nucleic acid joins with a complementary strand through base pairing" (Coombs J. (1994) *Dictionary of Biotechnology*, Stockton Press, New York N.Y.) as well as the process of amplification as carried out in polymerase chain reaction technologies as described in Dieffenbach C. W. and G. S. Dveksler (1995, *PCR Primer, a Laboratory Manual*, Cold Spring Harbor Press, Plainview N.Y.) and incorporated herein by reference.

As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring CN PDE.

As used herein "substitution" results from the replacement of one or more nucleotides or amino acids by different nucleotides or amino acids, respectively.

Altered cn pde8 polynucleotide sequences which may be used in accordance with the invention include deletions, insertions or substitutions of different nucleotide residues resulting in a polynucleotide that encodes the same or a functionally equivalent CN PDE. The protein may also show deletions, insertions or substitutions of amino acid residues which produce a silent change and result in a functionally equivalent CN PDE. Deliberate amino acid substitutions may be made on the basis of similarity in polarity, charge, solubility, hydrophobicity, hydrophilicity, and/or the amphipathic nature of the residues as long as the biological activity of CN PDE is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of CN PDE. As used herein, an "allele" or "allelic sequence" is an alternative form of CN PDE. Alleles result from a mutation, ie. a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a CN PDE coding sequence for a variety of reasons, including but not limited to, alterations which modify the cloning, processing and/or expression of the gene product. For example, mutations may be introduced using techniques which are well known in the art, eg. site-directed mutagenesis to insert new restriction sites, to alter glycosylation patterns or to change codon preference.

In another embodiment of the invention, a CN PDE natural, modified or recombinant sequence may be ligated to a heterologous sequence to encode a fusion protein. For example, for screening of peptide libraries for inhibitors of CN PDE activity, it may be useful to encode a chimeric CN PDE protein expressing a heterologous epitope that is recognized by a commercially available antibody. A fusion protein may also be engineered to contain a cleavage site located between a CN PDE sequence and the heterologous protein sequence, so that the CN PDE may be cleaved and purified away from the heterologous moiety.

In an alternate embodiment of the invention, the coding sequence of CN PDE could be synthesized, whole or in part, using chemical methods well known in the art (see Caruthers M. H. et al (1980) Nuc Acids Res Symp Ser 215–23, Horn T. et al (1980) Nuc Acids Res Symp Ser 225–32, etc). Alternatively, the protein itself could be produced using chemical methods to synthesize a CN PDE amino acid sequence, whole or in part. For example, peptides can be synthesized by solid phase techniques, cleaved from the resin, and purified by preparative high performance liquid chromatography (eg. Creighton (1983) Proteins Structures And Molecular Principles, WH Freeman and Co, New York N.Y.). The composition of the synthetic peptides may be confirmed by amino acid analysis or sequencing (eg. the Edman degradation procedure; Creighton, supra).

Direct peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer. Additionally, the amino acid sequence of CN PDE, or any part thereof, may be altered during direct synthesis and/or combined using chemical methods with sequence from other γ subunits, or any part thereof, to produce a variant polypeptide.

Identification of Transformants Containing Cn pde

Although the presence/absence of marker gene expression suggests that the gene of interest is also present, its presence and expression should be confirmed. For example, if the cn pde is inserted within a marker gene sequence, recombinant cells containing cn pde can be identified by the absence of marker gene function. Alternatively, a marker gene can be placed in tandem with a cn pde sequence under the control of a single promoter. Expression of the marker gene in response to induction or selection usually indicates expression of cn pde as well.

Alternatively, host cells which contain the coding sequence for cn pde and express cn pde may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the cn pde polynucleotide sequence can be detected by DNA-DNA or DNA-RNA hybridization or amplification using probes, portions or fragments of cn pde disclosed in SEQ ID NO:1. Nucleic acid amplification based assays involve the use of oligonucleotides or oligomers based on the cn pde sequence to detect transformants containing cn pde DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the cn pde nucleotide sequence shown in FIGS. 1A,1B,1C, and 1D.

A variety of protocols for detecting and measuring the expression of CN PDE polypeptide, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on CN PDE polypeptides is preferred, but a competitive binding assay may be employed. These and other assays are described, among other places, in Hampton R. et al (1990, Serological Methods, a Laboratory Manual, APS Press, St Paul Minn.) and Maddox D. E. et al (1983, J Exp Med 158:1211).

A wide variety of labels and conjugation techniques are known by those skilled in the art and can be used in various nucleic and amino acid assays. Means for producing labeled hybridization or PCR probes for detecting cn pde polynucleotide sequences include oligolabeling, nick translation, end-labeling or PCR amplification using a labeled nucleotide. Alternatively, the cn pde sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

Purification of CN PDE

Host cells transformed with a cn pde nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing cn pde can be designed with signal sequences which direct secretion of cn pde through a particular prokaryotic or eukaryotic cell membrane. Other recombinant constructions may join cn pde to nucleotide sequence encoding a polypeptide domain which will facilitate purification of soluble proteins (Kroll D. J. et al (1993) DNA Cell Biol 12:441–53; see also above discussion of vectors containing fusion proteins).

CN PDE may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J. (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and CN PDE is useful to facilitate purification.

Uses of CN PDE and Genetically Engineered Host Cells Containing CN PDE

The amino acid sequence of CN PDE 8A (SEQ ID NO:2) and CN PDE 8B (SEQ ID NO:4) is shown in FIGS. 1A,1B,1C,1D, and 2, respectively. The present invention encompasses amino acid sequences encoding other members from the CN PDE8 family which would include amino acid sequences having at least 60% identity to the amino acid sequence of SEQ ID NO:2. CN PDE8A disclosed herein appears to hydrolyze cyclic nucleotides based upon its homology to known phosphodiesterases, particularly in the 3' catalytic region known to be conserved among families of phosphodiesterases, and the presence of the motif "HDXXHXXXXN" from residue 200 to residue 209 of SEQ ID NO:2 which has been found in the catalytic domain of all PDEs isolated to date. Based upon the presence of polynucleotide sequences encoding CN PDE8A, or portions thereof, in cDNA libraries made from highly proliferative cells and hematopoietic cells, CN PDE8A disclosed herein appears to play a role in inflammation and/or immunomodulation and proliferation of cells through its regulation of the levels of cyclic nucleotides.

Accordingly, antagonists or inhibitors of CN PDE8A can be used to treat or ameliorate the symptoms of inflammation, conditions associated with proliferation of hematopoietic cells including leukemia or other myeloproliferative disease and HIV-infection. Such diseases include asthma, Alzheimer's disease, osteoarthritis and artherosclerosis, ischemia, psoriasis, lymphomatoid granulomatosis, allergies, leukemias and myeloproliferative diseases, HIV infection and autoimmune diseases, such as rheumatoid arthritis, myasthenia gravis and diabetes. Such inhibitors or antagonists can be administered alone or in combination with other therapeutics for the treatment of such diseases. For example, an antagonist of CN PDE administered to individuals with HIV-1 infection may have the effect of increasing T-cell counts. Furthermore, antagonists of CN PDE may be used therapeutically to ameliorate the symptoms associated with inflammation such as swelling and pain.

Alternatively, agonists or other agents capable of elevating levels of a CN PDE8A may be administered to individuals having conditions associated with immunosuppression, such as Severe Combined Immunodeficiency Disease (SCID), drug induced immunosuppression, eg chemotherapy and cyclosporin therapy for individuals undergoing organ or tissue transplant; and acute or chronic infections, such as septic shock and other bacterial and fungal infections, including Staphylococcal and Aspergillus infections. Such agonists can be administered alone or in combination with other therapeutics for the treatment of such diseases.

In an embodiment of the present invention, CN PDE8 or a variant thereof and/or a cell line that expresses the CN PDE8 or variant thereof may be used to screen for antibodies, peptides, or other molecules, such as organic or inorganic molecules, that act as modulators of phosphodiesterase activity, thereby identifying a therapeutic capable of modulating cyclic nucleotide levels. For example, anti-CN PDE8 antibodies capable of neutralizing the activity of CN PDE8 may be used to inhibit CN PDE8 hydrolysis of cyclic nucleotides, thereby increasing their constitutive levels. Alternatively, screening of peptide libraries or organic libraries made by combinatorial chemistry with recombinantly expressed CN PDE8 or variants thereof or cell lines expressing CN PDE8 or variants thereof may be useful for identification of therapeutic molecules that function by modulating CN PDE8 hydrolysis of cyclic nucleotides. Synthetic compounds, natural products, and other sources of potentially biologically active materials can be screened in a number of ways deemed to be routine to those of skill in the art. For example, nucleotide sequences encoding the N-terminal region of CN PDE8A may be expressed in a cell line which can be used for screening of allosteric modulators, either agonists or antagonists, of CN PDE8A activity. Alternatively, nucleotide sequences encoding the conserved catalytic domain of CN PDE8A can be expressed in cell lines and used to screen for inhibitors of cyclic nucleotide hydrolysis.

The ability of a test molecule to interfere with CN PDE8 activity or cyclic nucleotide hydrolysis may be determined by measuring cyclic nucleotide levels or CN PDE8 levels as disclosed in Smith et al. (1993 Appl. Biochem. Biotechnol. 41:189–218). There are also commercially available immunoassay kits for the measurement of cAMP and cGMP (e.g. Amersham International, Arlington Heights, Ill. and DuPont, Boston Mass.). The activity of CN PDE8 may also be monitored by measuring other responses such as phosphorylation or dephosphorylation of other proteins using conventional techniques developed for these purpose.

Accordingly, the present invention provides a method of identifying a compound which is capable of modulating the cyclic nucleotide phosphodiesterase activity of a CN PDE8, or a fragment thereof, comprising the steps of a)contacting the compound with a CN PDE8, or a fragment thereof; b)incubating the mixture of step a) with a cyclic nucleotide under conditions suitable for the hydrolysis of the cyclic nucleotide; c) measuring the amount of cyclic nucleotide hydrolysis; and d) comparing the amount of cyclic nucleotide hydrolysis of step c) with the amount of cyclic nucleotide hydrolysis obtained with the CN PDE8, or a fragment thereof, incubated without the compound, thereby determining whether the compound stimulates or inhibits cyclic nucleotide hydrolysis. In one embodiment of the method, the fragment is from the N-terminal region of the CN PDE8 and provides a method to identify allosteric modulators of the CN PDE8. In another embodiment of the present invention, the fragment is from the carboxy terminal region of the CN PDE8 and provides a method to identify inhibitors of cyclic nucleotide hydrolysis.

CN PDE Antibodies

Procedures well known in the art may be used for the production of antibodies to CN PDE8 polypeptides. Such antibodies include, but are not limited to, polyclonal, monoclonal, chimeric, single chain, Fab fragments and fragments produced by a Fab expression library. Neutralizing antibodies, ie, those which inhibit biological activity of CN PDE polypeptides, are especially preferred for diagnostics and therapeutics.

For the production of antibodies, various hosts including goats, rabbits, rats, mice, etc may be immunized by injection with CN PDE8 polypeptide or any portion, fragment or oligopeptide which retains immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants which may be employed if purified CN PDE polypeptide is administered to immunologically compromised individuals for the purpose of stimulating systemic defense.

Monoclonal antibodies to CN PDE8 polypeptide may be prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce CN PDE specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86:3833–3837), and Winter G. and Milstein C. (1991; Nature 349:293–299).

Antibody fragments which contain specific binding sites for CN PDE8 may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W. D. et al (1989) Science 256:1275–1281).

CN PDE8-specific antibodies are useful for the diagnosis of conditions and diseases associated with expression of CN PDE8 polypeptide. A variety of protocols for competitive binding or immunoradiometric assays using either polyclonal or monoclonal antibodies with established specificities are well known in the art. Such immunoassays typically involve the formation of complexes between CN PDE polypeptides and its specific antibody (or similar CN PDE8-binding molecule) and the measurement of complex formation. A two-site, monoclonal-based immunoassay utilizing monoclonal antibodies reactive to two noninterfering epitopes on a specific CN PDE8 protein is preferred, but a competitive binding assay may also be employed. These assays are described in Maddox D. E. et al (1983, J Exp Med 158:1211).

Diagnostic Assays Using Cn pde Specific Antibodies

Anti-CN PDE8 antibodies are useful for the diagnosis of inflammation, conditions associated with proliferation of hematopoietic cells and HIV infection or other disorders or diseases characterized by abnormal expression of a CN PDE8. Diagnostic assays for a CN PDE8 include methods utilizing the antibody and a label to detect a CN PDE8 polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule. A wide variety of reporter molecules are known to those of skill in the art.

A variety of protocols for measuring a CN PDE8 polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on a CN PDE8 polypeptide is preferred, but a competitive binding assay may be employed. These assays are described, among other places, in Maddox, D. E. et al (1983, J Exp Med 158:1211).

In order to provide a basis for the diagnosis of disease, normal or standard values from a CN PDE8 polypeptide expression must be established. This is accomplished by combining body fluids or cell extracts taken from normal subjects, either animal or human, with antibody to a CN PDE8 polypeptide under conditions suitable for complex formation which are well known in the art. The amount of standard complex formation may be quantified by comparing it with a dilution series of positive controls where a known amount of antibody is combined with known concentrations of a purified CN PDE8 polypeptide. Then, standard values obtained from normal samples may be compared with values obtained from samples from subjects potentially affected by a disorder or disease related to a CN PDE8 polypeptide expression. Deviation between standard and subject values establishes the presence of the disease state.

Drug Screening

A CN PDE8 polypeptide, its immunogenic fragments or oligopeptides thereof can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between a CN PDE8 polypeptide and the agent being tested, may be measured. Accordingly, the present invention provides a method for screening a plurality of compounds for specific binding affinity with a CN PDE8, or a portion thereof, comprising providing a plurality of compounds; combining a ON PDE8 or a portion thereof with each of a plurality of compounds for a time sufficient to allow binding under suitable conditions; and detecting binding of a CN PDE8, or portion thereof, to each of the plurality of compounds, thereby identifying the compounds which specifically bind a CN PDE8. In such an assay, the plurality of compounds may be produced by combinatorial chemistry techniques known to those of skill in the art.

Another technique for drug screening provides for high throughput screening of compounds having suitable binding affinity to the CN PDE8 polypeptides and is described in detail in Geysen, European Patent Application 84/03564, published on Sep. 13, 1984, incorporated herein by reference. In summary, large numbers of different small peptide test compounds are synthesized on a solid substrate, such as plastic pins or some other surface. The peptide test compounds are reacted with CN PDE8 fragments and washed. A bound CN PDE8 is then detected by methods well known in the art. A purified CN PDE8 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding a CN PDE8 specifically compete with a test compound for binding a ON PDE8. In this manner, the antibodies can be used to detect the presence of any peptide which shares one or more antigenic determinants with a CN PDE8.

Uses of Cn pde Polynucleotide

A cn pde8 polynucleotide, or any part thereof, may provide the basis for diagnostic and/or therapeutic compounds. For diagnostic purposes, cn pde8 polynucleotide sequences may be used to detect and quantitate gene expression in conditions, disorders or diseases in which cn pde8 activity may be implicated, for example, in inflammation, conditions associated with proliferation of hematopoietic cells and HIV infection. For therapeutic purposes, cn pde8 antisense molecules may be administered to individuals with inflammation, conditions associated with proliferation of hematopoietic cells and HIV infection. Alternatively, for therapeutic purposes, polynucleotide sequences of cn pde8 may be administered to individuals having acute or chronic infection or being immunosuppressed where it would be desirable to enhance the immune response.

Included in the scope of the invention are oligonucleotide sequences, antisense RNA and DNA molecules and ribozymes, which function to destabilize cn pde8 mRNA or inhibit translation of a cn pde8. Such nucleotide sequences may be used in conditions where is would be preferable to increase cyclic nucleotide levels, such as in inflammation.

Another aspect of the subject invention is to provide for nucleic acid hybridization or PCR probes which are capable of detecting polynucleotide sequences, including genomic sequences, encoding cn pde or closely related molecules, such as alleles. The specificity of the probe, ie, whether it is derived from a highly conserved, conserved or non-conserved region or domain, and the stringency of the hybridization or amplification (high, intermediate or low) will determine whether the probe identifies only naturally occurring cn pde, or related sequences. Probes for the detection of related nucleic acid sequences are selected from conserved or highly conserved nucleotide regions of cyclic nucleotide PDE family members, such as the 3' region, and such probes may be used in a pool of degenerate probes. For the detection of identical nucleic acid sequences, or where maximum specificity is desired, nucleic acid probes are selected from the non-conserved nucleotide regions or unique regions of cn pde polynucleotides. As used herein, the term "non-conserved nucleotide region" refers to a nucleotide region that is unique to the cn pde disclosed herein and does not occur in related family members, such as known cyclic nucleotide PDEs.

Diagnostic Uses of Cn pde Polynucleotide

A CN PDE8 encoding polynucleotide sequence may be used for the diagnosis of diseases resulting from expression of CN PDE8 associated with inflammation, conditions associated with proliferation of hematopoietic cells, or HIV infection. For example, polynucleotide sequences encoding CN PDE8A may be used in hybridization or PCR assays of tissues from biopsies or autopsies or biological fluids, such as serum, synovial fluid or tumor biopsy, to detect abnormalities in CN PDE8A expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for cn pde expression must be established. This is accomplished by combining body fluids or cell extracts taken from normal subjects, either animal or human, with cn pde8a or a portion thereof, under conditions suitable for hybridization or amplification. Standard hybridization may be quantified by comparing the values obtained for normal subjects with a dilution series of positive controls run in the same experiment where a known amount of purified cn pde8a is used. Standard values obtained from normal samples may be compared with values obtained from samples from subjects potentially affected by a disorder or disease related to cn pde expression. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

PCR as described in U.S. Pat. Nos. 4,683,195; 4,800,195; and 4,965,188 provides additional uses for oligonucleotides based upon the cn pde8a sequence. Such oligomers are generally chemically synthesized, but they may be generated enzymatically or produced form a recombinant source. Oligomers generally comprise two nucleotide sequences, one with sense orientation (5'→3') and one with antisense (3'←5') employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally methods to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the an oligomer of interest is presented in various dilutions and a spectrophotometric or colorimetric response gives rapid quantitation.

Therapeutic Uses of a Cn pde Polynucleotide

A cn pde8a antisense molecule may provide the basis for treatment of various abnormal conditions related to inflammation and conditions associated with proliferation of hematopoietic cells and HIV infection where it would be desirable to decrease the immune response. In such conditions it would be desirable to decrease the levels of cytokines, such as TNF-alpha. Alternatively, polynucleotide sequences encoding cn pde8a may provide the basis for the treatment of various abnormal conditions related to acute and chronic infection, such as septic shock, and immunosuppression, such as SCID, where it would be desirable to increase the immune response.

Expression vectors derived from retroviruses, adenovirus, herpes or vaccinia viruses, or from various bacterial plasmids, may be used for delivery of recombinant cn pde8 sense or antisense molecules to the targeted cell population. Methods which are well known to those skilled in the art can be used to construct recombinant vectors containing cn pde8. See, for example, the techniques described in Maniatis et al (supra) and Ausubel et al(supra). Alternatively, recombinant cn pde8 can be delivered to target cells in liposomes.

The full length cDNA sequence and/or its regulatory elements enable researchers to use a cn pde8 as a tool in sense (Youssoufian H. and H. F. Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions.

Additionally, on pde8 expression can be modulated by transfecting a cell or tissue with expression vectors which express high levels of a cn pde8A fragment in conditions where it would be preferable to block phosphodiesterase activity thereby increase cyclic nucleotide levels. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector (Mettler I., personal communication) and even longer if appropriate replication elements are part of the vector system.

Modifications of gene expression can be obtained by designing antisense sequences to the control regions of the cn pde gene, such as the promoters, enhancers, and introns. Oligonucleotides derived from the transcription initiation site, eg. between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of cn pde RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridization with complementary oligonucleotides using ribonuclease protection assays.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Methods for introducing vectors into cells or tissue include those methods discussed infra. In addition, several of these transformation or transfection methods are equally suitable for the ex vivo therapy.

Furthermore, the cn pde polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.
Detection and Mapping of Polynucleotide Sequences Related to Cn pde The nucleic acid sequence for cn pde8 can also be used to generate hybridization probes as previously described, for mapping the endogenous genomic sequence. The sequence may be mapped to a particular chromosome or to a specific region of the chromosome using well known techniques. These include in situ hybridization to chromosomal spreads (Verma et al (1988) *Human Chromosomes: A Manual of Basic Techniques*, Pergamon Press, New York City), flow-sorted chromosomal preparations, or artificial chromosome constructions such as YACs, bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc between normal, carrier or affected individuals.

Pharmaceutical Compositions

The present invention relates to pharmaceutical compositions which may comprise all or portions of cn pde8 polynucleotide sequences, cn pde8 antisense molecules, CN PDE8 polypeptides, protein, peptide or organic modulators of CN PDE8 bioactivity, such as inhibitors, antagonists (including antibodies) or agonists, alone or in combination with at least one other agent, such as stabilizing compound, and may be administered in any sterile, biocompatible pharmaceutical carrier, including, but not limited to, saline, buffered saline, dextrose, and water.

Cn pde8 nucleotide and CN PDE8 amino acid sequences can be administered to a patient alone, or in combination with other nucleotide sequences drugs or hormones or in pharmaceutical compositions where it is mixed with excipient(s) or other pharmaceutically acceptable carriers. In one embodiment of the present invention, the pharmaceutically acceptable carrier is pharmaceutically inert. A preferred route of administration for treatment of inflammation would be local delivery for localized inflammation, such as arthritis, and intravenous delivery for systemic conditions, such as acute infection or SCID.

Cn pde antisense molecules or antagonist or inhibitors of CN PDE may be administered alone to individuals having conditions associated with inflammation, cancer or HIV infection or in combination with other types of agents or therapy including other anti-inflammatory agents, chemotherapeutics or radiation therapy for example.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art.

The pharmaceutical compositions can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of CN PDE8 may be that amount that ameliorates the symptoms of inflammation such as swelling or pain. Determination of effective amounts is well within the capability of those skilled in the art, especially in light of the disclosure provided below.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, eg, by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of CN PDE8, conditions indicated on the label may include treatment of inflammation, cancer or HIV infection.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models to achieve a desirable circulating concentration range that adjusts CN PDE8 levels.

A therapeutically effective dose refers to that amount of CN PDE8 which ameliorates symptoms of the particular disease or condition. Toxicity and therapeutic efficacy of such compounds can be determined by standard pharmaceutical procedures in cell cultures or experimental animals, eg. for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. No. 4,657,760; 5,206,344; or 5,225,212. Those skilled in the art will employ different formulations for CN PDE than for the inhibitors of CN PDE. Administration to the bone marrow may necessitate delivery in a manner different from intravenous injections.

These examples are provided by way of illustration and are not included for the purpose of limiting the invention.

EXAMPLES

I CONSTRUCTION OF THP1PLB02 LIBRARY AND ISOLATION OF cDNA CLONES

THP-1 is a human leukemic cell line derived from the blood of a 1-year-old boy with acute monocytic leukemia. Cells used for the PMA-induced library were cultured for 48 hr with 100 nm PMA diluted in DMSO and for the PMA+LPS library were cultured for 48 hr with 100 nm PMA in DMSO and for 4 hr with 1 µg/ml LPS. The control THP-1 cells represent monocytes, PMA-induced cells represent macrophages, and PMA+LPS-stimulated cells represent activated macrophages. All three cDNA libraries—control, PMA induced, and PMA+LPS stimulated—were custom constructed by Stratagene (Stratagene, 11099 M. Torrey Pines Rd., La Jolla, Calif. 92037) essentially as described below.

Stratagene prepared the cDNA library using oligo d(T) priming. Synthetic adapter oligonucleotides were ligated onto the cDNA molecules enabling them to be inserted into the UNIZAP™ vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the PBLUESCRIPT® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-BLUE® (Stratagene). The high transformation efficiency of this bacterial strain increases the probability that the cDNA library will contain rare, under-represented clones. Alternative unidirectional vectors include, but are not limited to, pcDNAI (Invitrogen, San Diego Calif.) and pSHIox-1 (Novagen, Madison Wis.).

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 Plasmid Purification System from the QIAGEN® DNA Purification System (QIAGEN Inc, Chatsworth Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

The cDNA inserts from random isolates of the THP-1 library were sequenced in part.

II Homology Searching of cDNA Clones and Their Deduced Proteins

Each cDNA was compared to sequences in GenBank using a BLAST search (Basic Local Alignment Search Tool; Altschul S. F. (1993) J. Mol. Evol. 36: 290–300; Altschul S. F. et al (1990) J. Mol. Biol. 215:403–410) comparing the cDNAs of the THP-1 library (INCYTE library THP1PLB02) against the primate database of GenBank 91. This method identified Incyte Clone 156196 as a non-exact match to rat cn pde (NCBI GI 409816) which appears to be a member of family 3 or 4 cyclic phosphodiesterases.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

CN PDE was identified using the ABI INHERIT™ DNA Analysis System (Perkin Elmer, Norwalk, Conn.) software which identified clone 156196 as being related to cyclic nucleotide phosphodiesterase in Genbank, GI number 409816. PCR extension analysis using primers designed from 156196 was performed. The nucleotide sequences generated by PCR extension analysis were assembled using the ABI Assembler Applications part of the INHERIT™ DNA Analysis System (Perkin Elmer, Norwalk, Conn.) which creates and manages sequence assembly projects by assembling overlapping sequence fragments into a larger nucleotide sequence. The polynucleotide and amino acid sequence of CN PDE are disclosed herein in FIGS. 1A,1B, 1C, and 1D (SEQ ID NO:1) and (SEQ ID NO:2), respectively.

III DETERMINATION OF READING FRAME OF cDNA CLONE

The reading frame of individual cDNA clones obtained from the THP1PLB02 library was obtained by analyzing the polynucleotide sequences for the presence of start (ATG, GTG, etc.) and stop codons (TGA, TAA, TAG). Typically, one frame will continue throughout the major portion of all of a cDNA sequence and the other two pending frames tend to contain numerous stop codons. Algorithms for determining reading frame have been developed which analyze the occurrence of individual nucleotide bases of each putative codon triplet (e.g., Fickett, J. W. Nucleic Acids Research, 10, 5303 (1982)). Coding DNA tends to contain predominantly certain nucleotides within certain triplet periodicities, such as a significant preference for pyrimidines in the third codon position. These algorithms have been incorporated into widely available software and can be easily used to determine coding potential (and frame) of a given stretch of DNA. This algorithm-derived information, combined with start/stop codon information, was used to determine proper frame of individual clones within the THP1PLB02 library with a high degree of certainty, thus permitting the correct reading frame alignment with appropriate expression vehicles.

IV Extension of Cn pde to Recover Regulatory Elements

The nucleic acid sequence of cn pde may be used to design oligonucleotide primers for obtaining full length sequences from genomic libraries. One primer is synthesized to initiate extension in the antisense direction (XLR) and the other is synthesized to extend sequence in the sense direction (XLF). The primers allow the known cn pde sequence to be extended 37 outward" generating amplicons containing new, unknown nucleotide sequence for the control region of interest. The initial primers are designed from the cDNA using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

A human genomic library is used to extend and amplify 5' upstream sequence. If necessary, a second set of primers is designed to further extend the known region. By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J. et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

V Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi of [γ-$^{32}$Pd] adenosine triphosphate (Amersham, Chicago Ill.) and T4 polynucleotide kinase (DuPont NEN®, Boston, Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, BgI II, EcoR I, Pst I, Xba 1, or Pvu II; DuPont NEN®).

The DNA from each digest is fractionated on a 0.7 percent agarose gel and transferred to nylon membranes Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI Antisense Molecules

The cn pde sequence, or any part thereof, may be used to inhibit in vivo or in vitro expression of endogenous cn pde. Although use of antisense oligonucleotides, consisting of about 20 base-pairs, is specifically described, essentially the same procedure may be used with larger cDNA fragments. An oligonucleotide based on the coding sequence of cn pde may be used to inhibit expression of endogenous cn pde. Using Oligo 4.0, the complementary oligonucleotide can be designed from the conserved 5' sequence and used either to inhibit transcription by preventing promoter binding to the upstream nontranslated sequence or translation of an cn pde transcript by preventing the ribosome from binding to the mRNA.

VII Production of CN PDE Specific Antibodies

For production of polyclonal antibodies, the deduced amino acid sequence of CN PDE is analyzed using DNAS-TAR software (DNASTAR Inc) to determine regions of high immunogenicity and a corresponding oligopeptide is synthesized and used to raise antibodies in rabbits. Analysis to select appropriate epitopes, such as those near the C-terminus or in adjacent hydrophilic regions is described by Ausubel F. M. et al (supra). An oligopeptide of about 15 residues in length is synthesized using an ABI Peptide Synthesizer Model 431A (Perkin Elmer, Norwalk, Conn.) using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

VIII Purification of CN PDE Using Specific Antibodies

Endogenous or recombinant CN PDE can be purified by immunoaffinity chromatography using antibodies specific for CN PDE. An immunoaffinity column is constructed by covalently coupling CN PDE antibody to an activated chromatographic resin such as CnBr-activated Sepharose (Pharmacia Biotech). After the coupling, the resin is blocked and washed according to the manufacturer's instructions.

Media containing CN PDE is passed over the immunoaffinity column, and the column is washed under conditions that allow the preferential absorbance of CN PDE (eg, high ionic strength buffers in the presence of detergent). The column is eluted under conditions that disrupt antibody/CN PDE binding (eg, a buffer of pH 2–3 or a high concentration of a chaotrope such as urea or thiocyanate ion), and CN PDE is collected.

IX Identification of Molecules Which Interact with Cn pde

CN PDE8A, or biologically active fragments thereof, is labeled with $^{125}$I Bolton-Hunter reagent (Bolton, A. E. and Hunter, W. M. (1973) Biochem J 133:529). Candidate small molecules previously arrayed in the wells of a 96 well plate are incubated with the labeled CN PDE8A, washed and any wells with labeled CN PDE8A complex are assayed. Data obtained using different concentrations of CN PDE are used to calculate values for the number, affinity, and association of CN PDE with the candidate molecules.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. A purified polynucleotide consisting of a nucleic acid sequence encoding the CN PDE8 polypeptide having the sequence shown in SEQ ID NO:2.

2. The purified polynucleotide of claim 1 wherein the nucleic acid sequence consists of the sequence shown in SEQ ID NO:1.

3. A purified polynucleotide consisting of a nucleic acid sequence encoding the CN PDE8 polypeptide having the sequence shown in SEQ ID NO:4.

4. The purified polynucleotide of claim 3 wherein the nucleic acid sequence consists of the sequence shown in SEQ ID NO:3.

5. An expression vector comprising the polynucleotide of claim 1.

6. A host cell transformed with the expression vector of claim 5.

7. A method for producing the polypeptide having the CN PDE8 amino acid sequence shown in SEQ ID NO:2, the method comprising the steps of:

a) culturing the host cell of claim 6 to allow expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2229 base pairs (B) TYPE: nucleic acid
(C) STRANDEDNESS: single
(D) TOPOLOGY: linear (i i) MOLECULE TYPE: cDNA (v i i) IMMEDIATE SOURCE:
(A) LIBRARY: THP-1 CELLS
(B) CLONE: 156196

(x i) SEQUENCE DESCRIPTION: SEQ ID NO:1:

| | | | | | | |
|---|---|---|---|---|---|---|
| CGATACTATA | AATTCATGCA | TCAGGATAGG | CAAGGAGTGG | CAAGGAATTT | ACTATGCCAA | 60 |
| AAAGAAAAAC | GGAGATAATA | TACAACAAAA | TGTGAAGATA | ATACCTGTCA | TTGGACAGGG | 120 |
| AGGAAAAATT | AGACACTATG | TGTCCATTAT | CAGAGTGTGC | AATGGCAACA | ATAAGGCTGA | 180 |
| GAAAATATCC | GAATGTGTTC | AGTCTGACAC | TCATACAGAT | AATCAGACAG | GCAAACATAA | 240 |
| AGACAGGAGA | AAAGGCTCAC | TAGACGTCAA | AGCTGTTGCC | TCCCGTGCAA | CTGAAGTTTC | 300 |
| CAGCCAGAGA | CGACACTCTT | CCATGGCCCG | GATACATTCC | ATGACAATTG | AGGCGCCCAT | 360 |
| CACCAAGGTA | ATCAATATTA | TCAATGCTGC | CCAGGAAAGT | AGTCCATGC | CTGTGACAGA | 420 |
| AGCCCTAGAC | CGTGTGCTGG | AAATTCTAAG | AACCACTGAG | TTATATTCAC | CACAGTTTGG | 480 |
| TGCTAAAGAT | GATGATCCCC | ATGCCAATGA | CCTTGTTGGG | GGCTTAATGT | CTGATGGTTT | 540 |
| GCGAAGACTA | TCAGGGAATG | AATATGTTCT | TTCAACAAAA | AACACTCAAA | TGGTTTCAAG | 600 |
| CAATATAATC | ACTCCCATCT | CCCTTGATGA | TGTCCCACCA | CGGATAGCTC | GGGCCATGGA | 660 |
| AAATGAGGAA | TACTGGGACT | TTGATATTTT | TGAACTGGAG | GTTGCCACCC | ACAATAGGCC | 720 |
| TTTGATTTAT | CTTGGTCTCA | AAATGTTTGC | TCGCTTTGGA | ATCTGTGAAT | TCTTACACTG | 780 |
| CTCCGAGTCA | ACGCTAAGAT | CATGGTTACA | AATTATCGAA | GCCAATTATC | ATTCCTCCAA | 840 |
| TCCCTACCAC | AATTCTACAC | ATTCTGCTGA | TGTGCTTCAT | GCCACTGCCT | ATTTTCTCTC | 900 |
| CAAGGAGAGG | ATAAAGGAAA | CTTTAGATCC | AATTGATGAG | GTCGCTGCAC | TCATCGCAGC | 960 |
| CACCATTCAT | GATGTGGATC | ACCCTGGGAG | AACCAACTCC | TTCCTGTGTA | ATGCTGGAAG | 1020 |
| TGAGCTGGCC | ATTTTGTACA | ATGACACTGC | TGTGCTGGAG | AGCCACCATG | CGGCCTTGGC | 1080 |
| CTTCCAGCTG | ACCACTGGAG | ATGATAAATG | CAATATATTT | AAAAACATGG | AGAGGAATGA | 1140 |
| TTATCGGACA | CTGCGCCAGG | GGATTATCGA | CATGGTCTTA | GCCACAGAAA | TGACAAGGCA | 1200 |
| CTTTGAGCAT | GTCAACAAAT | TTGTCAACAG | CATCAACAAA | CCCTTGGCAA | CACTAGAAGA | 1260 |
| AAATGGGGAA | ACTGATAAAA | ACCAGGAAGT | GATAAACACT | ATGCTTAGGA | CTCCAGAGAA | 1320 |
| CCGGACCCTA | ATCAAACGAA | TGCTGATTAA | ATGTGCTGAT | GTGTCCAATC | CCTGCCGACC | 1380 |
| CCTGCAGTAC | TGCATCGAGT | GGGCTGCACG | CATTTCGGAA | GAATATTTTT | CTCAGACTGA | 1440 |
| TGAAGAGAAG | CAGCAGGGCT | TACCTGTGGT | GATGCCAGTG | TTTGACAGAA | ATACCTGCAG | 1500 |
| CATCCCCAAA | TCCCAAATCT | CTTTCATTGA | TTACTTCATC | ACAGACATGT | TGATGCTTG | 1560 |
| GGATGCCTTT | GTAGACCTGC | CTGATTTAAT | GCAGCATCTT | GACAACAACT | TTAAATACTG | 1620 |
| GAAAGGACTG | GACGAAATGA | AGCTGCGGAA | CCTCCGACCA | CCTCCTGAAT | AGTGGGAGAC | 1680 |
| ACCACCCAGA | GCCCTGAAGC | TTTGTTCCTT | CGGTCATTTG | GAATTCCTGA | GGGCARACCA | 1740 |
| GAGCTCCTTG | GTCCTTTCAG | TRCWAGGCAG | NANACAGCCC | CCGATCTGYA | TAGCCTGTGA | 1800 |
| AAGCCCRCGG | GGACATCAGT | AACCTTCTKC | AGCCACCATC | CAATGCCATT | ACTGTCAAGT | 1860 |
| GAGACTTGGC | CMCTGTARCC | TGGGCCTKCT | KCAGGAGCTC | TTCAGAAAGG | CACATKAGGA | 1920 |
| CCACGGNTTT | SGCTCAGTTT | CTGGTAAAAC | ACAAGGTCTG | GAGTKCCCCT | GCMAAGGGTA | 1980 |
| TTGATGGACT | TCCTKCCAGT | GACAGAGCAT | GTCTATTTCC | AACAATTCTC | TCANTTACGT | 2040 |

```
TCAACACTTA AGAACGGCTA ATGGCAATAG GATCTTTAAC AACTTTTTCA CATCANAGNA     2100

GGTTCAATCG CTCACTTGGG NACACNACTG AGAGTGACTT CTCTTTTAAA ATTGAGTAAC     2160

AGATGGAAAA ATAAAATTTG GACTTGATTA TTAANATCCC NAANAAAAAA AAAAAAAAA     2220

AAAAAAAAA                                                             2229
```

( 2 ) INFORMATION FOR SEQ ID NO:2:

( i ) SEQUENCE CHARACTERISTICS:
        ( A ) LENGTH: 449 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: THP-1 CELLS
        ( B ) CLONE: 156196

( x i ) SEQUENCE DESCRIPTION: SEQ ID NO:2:

```
Met  Ala  Arg  Ile  His  Ser  Met  Thr  Ile  Glu  Ala  Pro  Ile  Thr  Lys  Val
 1              5                         10                       15

Ile  Asn  Ile  Ile  Asn  Ala  Ala  Gln  Glu  Ser  Ser  Pro  Met  Pro  Val  Thr
              20                        25                       30

Glu  Ala  Leu  Asp  Arg  Val  Leu  Glu  Ile  Leu  Arg  Thr  Thr  Glu  Leu  Tyr
             35                        40                        45

Ser  Pro  Gln  Phe  Gly  Ala  Lys  Asp  Asp  Pro  His  Ala  Asn  Asp  Leu
 50                        55                        60

Val  Gly  Gly  Leu  Met  Ser  Asp  Gly  Leu  Arg  Arg  Leu  Ser  Gly  Asn  Glu
 65                       70                        75                       80

Tyr  Val  Leu  Ser  Thr  Lys  Asn  Thr  Gln  Met  Val  Ser  Ser  Asn  Ile  Ile
                    85                        90                            95

Thr  Pro  Ile  Ser  Leu  Asp  Asp  Val  Pro  Pro  Arg  Ile  Ala  Arg  Ala  Met
                   100                      105                      110

Glu  Asn  Glu  Glu  Tyr  Trp  Asp  Phe  Asp  Ile  Phe  Glu  Leu  Glu  Val  Ala
              115                      120                      125

Thr  His  Asn  Arg  Pro  Leu  Ile  Tyr  Leu  Gly  Leu  Lys  Met  Phe  Ala  Arg
     130                      135                      140

Phe  Gly  Ile  Cys  Glu  Phe  Leu  His  Cys  Ser  Glu  Ser  Thr  Leu  Arg  Ser
145                      150                      155                      160

Trp  Leu  Gln  Ile  Ile  Glu  Ala  Asn  Tyr  His  Ser  Ser  Asn  Pro  Tyr  His
                   165                      170                      175

Asn  Ser  Thr  His  Ser  Ala  Asp  Val  Leu  His  Ala  Thr  Ala  Tyr  Phe  Leu
               180                      185                      190

Ser  Lys  Glu  Arg  Ile  Lys  Glu  Thr  Leu  Asp  Pro  Ile  Asp  Glu  Val  Ala
          195                      200                      205

Ala  Leu  Ile  Ala  Ala  Thr  Ile  His  Asp  Val  Asp  His  Pro  Gly  Arg  Thr
     210                      215                      220

Asn  Ser  Phe  Leu  Cys  Asn  Ala  Gly  Ser  Glu  Leu  Ala  Ile  Leu  Tyr  Asn
225                      230                      235                      240

Asp  Thr  Ala  Val  Leu  Glu  Ser  His  His  Ala  Ala  Leu  Ala  Phe  Gln  Leu
                    245                      250                      255

Thr  Thr  Gly  Asp  Asp  Lys  Cys  Asn  Ile  Phe  Lys  Asn  Met  Glu  Arg  Asn
               260                      265                      270

Asp  Tyr  Arg  Thr  Leu  Arg  Gln  Gly  Ile  Ile  Asp  Met  Val  Leu  Ala  Thr
          275                      280                      285

Glu  Met  Thr  Arg  His  Phe  Glu  His  Val  Asn  Lys  Phe  Val  Asn  Ser  Ile
```

|     |     |     |     | 290 |     |     |     | 295 |     |     |     | 300 |     |     |
|-----|-----|-----|-----|-----|-----|-----|-----|-----|-----|-----|-----|-----|-----|-----|
| Asn | Lys | Pro | Leu | Ala | Thr | Leu | Glu | Glu | Asn | Gly | Glu | Thr | Asp | Lys | Asn |
| 305 |     |     |     | 310 |     |     |     | 315 |     |     |     |     |     | 320 |
| Gln | Glu | Val | Ile | Asn | Thr | Met | Leu | Arg | Thr | Pro | Glu | Asn | Arg | Thr | Leu |
|     |     |     |     | 325 |     |     |     | 330 |     |     |     |     | 335 |     |
| Ile | Lys | Arg | Met | Leu | Ile | Lys | Cys | Ala | Asp | Val | Ser | Asn | Pro | Cys | Arg |
|     |     |     | 340 |     |     |     |     | 345 |     |     |     |     | 350 |     |
| Pro | Leu | Gln | Tyr | Cys | Ile | Glu | Trp | Ala | Ala | Arg | Ile | Ser | Glu | Glu | Tyr |
|     |     | 355 |     |     |     |     | 360 |     |     |     |     | 365 |     |     |
| Phe | Ser | Gln | Thr | Asp | Glu | Glu | Lys | Gln | Gln | Gly | Leu | Pro | Val | Val | Met |
|     |     | 370 |     |     |     | 375 |     |     |     | 380 |     |     |     |     |
| Pro | Val | Phe | Asp | Arg | Asn | Thr | Cys | Ser | Ile | Pro | Lys | Ser | Gln | Ile | Ser |
| 385 |     |     |     |     | 390 |     |     |     |     | 395 |     |     |     |     | 400 |
| Phe | Ile | Asp | Tyr | Phe | Ile | Thr | Asp | Met | Phe | Asp | Ala | Trp | Asp | Ala | Phe |
|     |     |     |     | 405 |     |     |     |     | 410 |     |     |     |     | 415 |     |
| Val | Asp | Leu | Pro | Asp | Leu | Met | Gln | His | Leu | Asp | Asn | Asn | Phe | Lys | Tyr |
|     |     |     | 420 |     |     |     |     | 425 |     |     |     |     | 430 |     |
| Trp | Lys | Gly | Leu | Asp | Glu | Met | Lys | Leu | Arg | Asn | Leu | Arg | Pro | Pro | Pro |
|     |     | 435 |     |     |     |     | 440 |     |     |     |     | 445 |     |     |
| Glu |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 245 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | |  |
|---|---|---|---|---|---|
| CATCAACAAG | CCAATGGCAG | CTGAGATTGA | AGGCAGCGAC | TGTGAATGCA | ACCCTGCTGG | 60 |
| GAAGAACTTC | CCTGNAAACC | AAATCCTGAT | CAAANGCATG | ATGATTAAGT | GTGCTGANGN | 120 |
| GGNCAACCCA | TGCCGACCCT | TGGACCTGTG | CATTGAATGG | GCTGGGAGGA | TCTCTGAGGA | 180 |
| GTATTTTGCA | CAGACTGATG | AAGAGAAGAG | ACAGGGACTA | CCTGTGGTGA | TGNCAGTGTT | 240 |
| TGACC | | | | | | 245 |

( 2 ) INFORMATION FOR SEQ ID NO:4:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: HEART
        ( B ) CLONE: 464655

( x i ) SEQUENCE DESCRIPTION: SEQ ID NO:4:

| Ile | Asn | Lys | Pro | Met | Ala | Ala | Glu | Ile | Glu | Gly | Ser | Asp | Cys | Glu | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Pro | Ala | Gly | Lys | Asn | Phe | Pro | Xaa | Asn | Gln | Ile | Leu | Ile | Lys | Xaa |
|     |     |     | 20  |     |     |     |     | 25  |     |     |     |     | 30  |     |     |
| Met | Met | Ile | Lys | Cys | Ala | Xaa | Xaa | Xaa | Asn | Pro | Cys | Arg | Pro | Leu | Asp |
|     |     |     | 35  |     |     |     | 40  |     |     |     |     | 45  |     |     |     |
| Leu | Cys | Ile | Glu | Trp | Ala | Gly | Arg | Ile | Ser | Glu | Glu | Tyr | Phe | Ala | Gln |
|     |     |     | 50  |     |     |     | 55  |     |     |     |     | 60  |     |     |     |

```
Thr  Asp  Glu  Glu  Lys  Arg  Gln  Gly  Leu  Pro  Val
65                  70                       75
```